(12) United States Patent
Hasler

(10) Patent No.: US 7,611,498 B2
(45) Date of Patent: Nov. 3, 2009

(54) ARRANGEMENT FOR THE COUPLING OF AN INTRAVENOUS TUBE WITH INFUSION PUMP

(75) Inventor: Roland Hasler, Bevaix (CH)

(73) Assignee: Codan Holding GmbH, Lensahn (DE)

( * ) Notice: Subject to any disclaimer, the term of this patent is extended or adjusted under 35 U.S.C. 154(b) by 313 days.

(21) Appl. No.: 11/436,907

(22) Filed: May 18, 2006

(65) Prior Publication Data
US 2007/0270765 A1 Nov. 22, 2007

(51) Int. Cl.
*A61M 5/00* (2006.01)
(52) U.S. Cl. .................. 604/250; 604/131; 604/151
(58) Field of Classification Search .............. 604/250, 604/131, 151, 246, 111
See application file for complete search history.

(56) References Cited

U.S. PATENT DOCUMENTS

| 5,017,192 | A | * | 5/1991 | Dodge et al. ............ 604/250 |
| 5,215,450 | A | * | 6/1993 | Tamari .................. 417/474 |
| 5,290,239 | A | * | 3/1994 | Classey et al. .......... 604/131 |
| 5,300,044 | A | * | 4/1994 | Classey et al. .......... 604/250 |
| 5,364,364 | A | * | 11/1994 | Kasvikis et al. ......... 604/151 |
| 5,401,256 | A | * | 3/1995 | Stone et al. ............ 604/250 |
| 5,567,120 | A | * | 10/1996 | Hungerford et al. ....... 417/63 |
| 6,117,115 | A | * | 9/2000 | Hill et al. .............. 604/250 |
| 6,261,262 | B1 | * | 7/2001 | Briggs et al. ............ 604/153 |
| 2002/0161333 | A1 | | 10/2002 | Luther .................. 604/167.01 |
| 2002/0165503 | A1 | | 11/2002 | Morris et al. ............ 604/250 |
| 2005/0033245 | A1 | * | 2/2005 | Abrahamson et al. ....... 604/250 |

FOREIGN PATENT DOCUMENTS

| EP | 0238227 | 9/1987 |
| WO | WO 96/30679 | 10/1996 |

* cited by examiner

*Primary Examiner*—Kevin C Sirmons
*Assistant Examiner*—Maria E Doukas
(74) *Attorney, Agent, or Firm*—Roberts & Roberts, LLP

(57) ABSTRACT

The invention concerns an arrangement to couple an intravenous hose having a roller clamp with an infusion pump. A hose clamp has clamping surfaces in the form of legs which can move relative one another about a hinge, the legs being enveloped on their outside by a biased clamping spring, and the device is formed by an expander rib that is fastened on the inside of the door and can be brought into engagement with the legs of the hose clamp so to produce the open position after closing the door to expand the legs. The housing has a receiver, into which the hose clamp can be snapped, and that a locking device is present in the housing that prevents the closing of the door if the hose clamp is not inserted into the receiver and permits the closing of the door when the hose clamp is fully inserted.

17 Claims, 15 Drawing Sheets

ARRANGEMENT FOR THE COUPLING OF AN INTRAVENOUS TUBE WITH INFUSION PUMP

BACKGROUND OF THE INVENTION

1. Field of the Invention

The invention concerns an arrangement for coupling an intravenous hose having a roller clamp with an infusion pump with a housing to deliver a medicinal solution to a patient.

2. Description of the Related Art

An arrangement for coupling an intravenous hose with an infusion pump is known from EP 238 227 B1. This, however, requires a clamping part with a drop-shaped opening, through which the hose passes and is moved back and forth in this drop-shaped opening by a device between the open and closed position. In addition, a locking device has to be provided on the pump to place the clamping part with the pump initially in the closed position. In the case of this prior known device the intravenous hose has to be first threaded through the drop-shaped opening, for which purpose the hose has to be released at one end of the infusion set. The intravenous hose can also be inserted into the housing of the infusion pump without the hose clamp and following this the door of housing can be closed. A person may have the impression that this arrangement is ready for operation, thus resulting in improper operation.

The provides the operators, such as carers, nurses and doctors with a system or an arrangement, or to improve the arrangement mentioned in the introduction in such a manner, that an uncontrolled delivery of infusion solutions of any kind to the patient will be ruled out. In other words, improper operations by the operating personnel should be prevented as far as possible.

According to the invention, the arrangement mentioned in the introduction will be achieved by that the hose clamp has clamping surfaces in the form of legs which can move relative one another about a hinge, the legs being enveloped on their outside by a biased clamping spring, and that the device is formed by an expander rib that is fastened on the inside of the door and can be brought into engagement with the legs of the hose clamp so that to produce the open position after closing the door to expand the legs, and that the housing has a receiver, into which the hose clamp can be snapped, and that a locking device is present in the housing that prevents the closing of the door if the hose clamp is not inserted into the receiver and permits the closing of the door when the hose clamp is fully inserted.

The arrangement according to the invention has also a simple construction and therefore can be produced economically, while it also ensures the exclusion of risk potential caused by improper operation.

In the following a preferred embodiment is explained in detail based on the drawing so that to achieve a better understanding of the invention. It has to be clarified, however, that the invention is not limited to this embodiment.

SUMMARY OF THE INVENTION

The invention provides an arrangement for coupling an intravenous hose having a roller clamp with an infusion pump with a housing to deliver a medicinal solution to a patient, comprising:

a hose clamp that can be coupled with the intravenous hose and can be displaced between an open position, in which the medicinal solution can flow through the hose, and a closed position, in which the hose is closed by the hose clamp, a device mounted on the door or lid of the housing, that can be engaged with the hose clamp to bring it to the open position from the closed position, wherein the hose clamp has clamping surfaces in the form of legs which can move relative one another about a hinge, the legs being enveloped on their outside by a biased clamping spring, wherein the device is formed by an expander rib that is fastened on the inside of the door and can be brought into engagement with the legs of the hose clamp so that to produce the open position after closing the door to expand the legs, wherein the housing has a receiver, into which the hose clamp can be snapped, and wherein a locking device is present in the housing that prevents the closing of the door if the hose clamp is not inserted into the receiver and permits the closing of the door when the hose clamp is fully inserted.

DETAILED DESCRIPTION OF THE INVENTION

Figure 1:
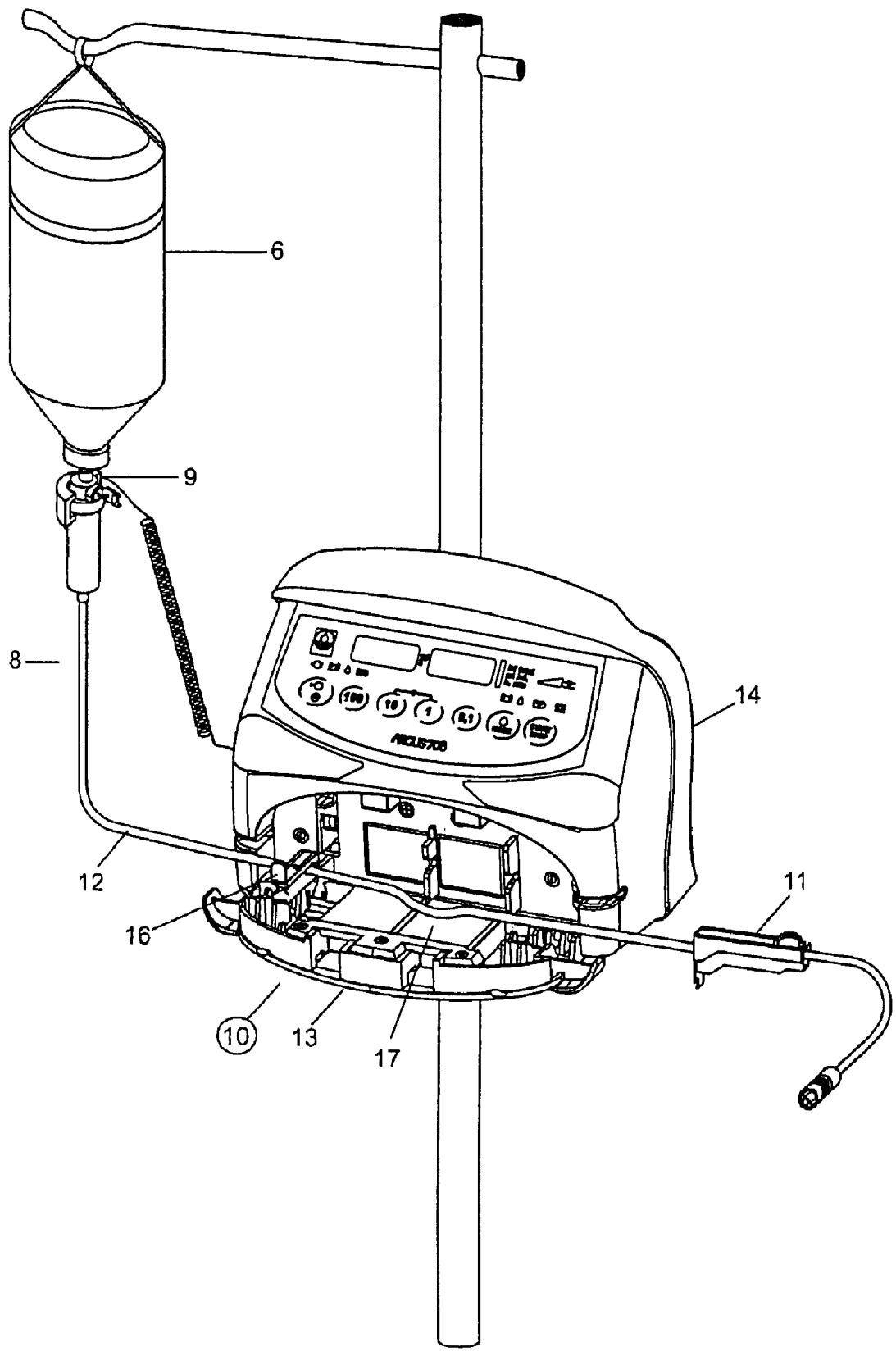
FIG. 1 is a perspective illustration of the arrangement according to the invention.
Figure 1A:
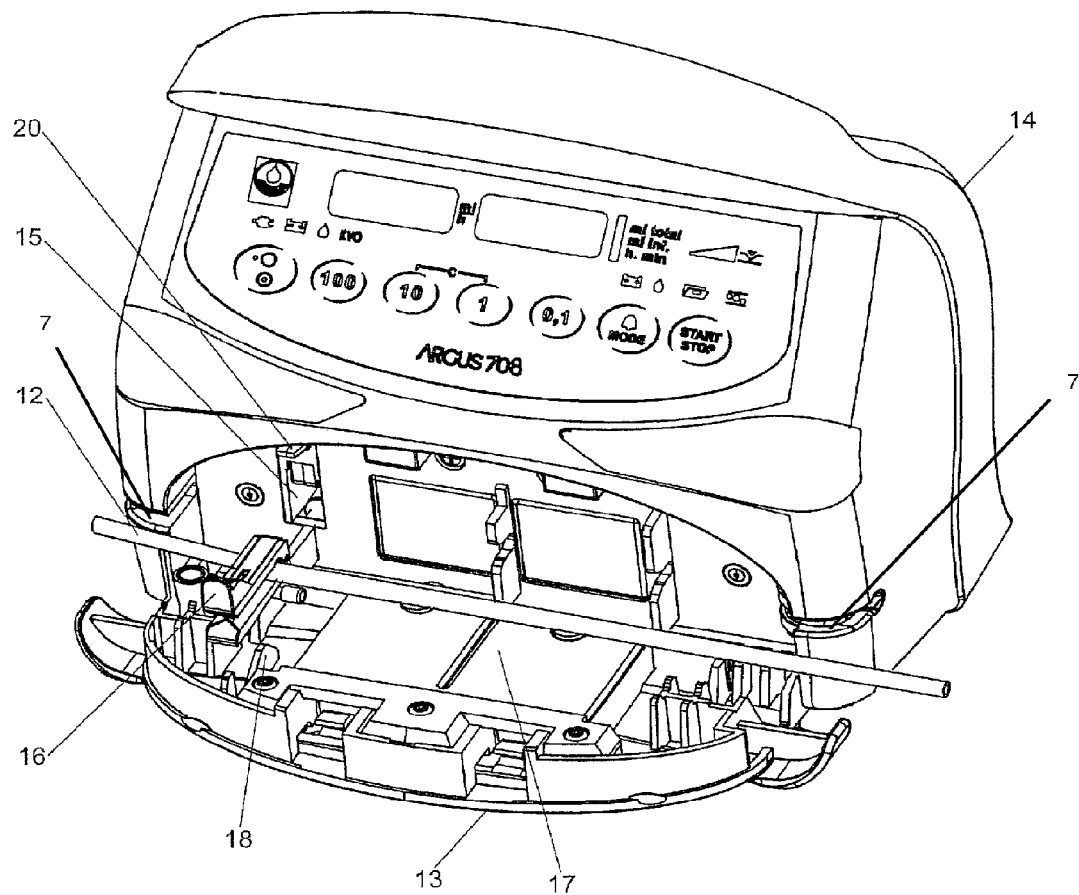
FIG. 1A is a perspective illustration of the arrangement according to the invention, with the door of the infusion pump open prior to starting up.

The overall arrangement according to the invention is designated in FIG. 1 by 10. It comprises the usual infusion set 8 with a drip chamber 9 having an insertion mandrel, that is inserted into an infusion flask 6 containing the medicinal solution, and a hose clamp 11 for the hose 12 and an infusion pump 14, provided in a housing. Horizontal hose guides 7 are provided in the housing both on the entry and outlet sides, as shown in FIG. 1A.

When using volumetric infusion pumps 14, the roller clamp 11 has only the function to clamp the hose 12 after the infusion has been prepared (connection of the infusion set with the infusion flask, filling and venting the set), so that to prevent the outflow of the fluid until the hose 12 is secured in the drive of the pump 14. After placing the hose 12 into the pump and closing the door 13 of the pump, the hose 12 is clamped by the combination of the peristaltic drive and the pressure plate 17. The roller clamp 11 of the infusion set is subsequently opened, and the system or the arrangement 10 is checked to see whether the pump 14 totally clamps the hose 12.

Thus during the feeding operation of the pump 14 the roller clamp 11 is fully open. If during the operation of the pump 14 a person opens the door 13 of the pump without previously closing the roller clamp 11, will bring with it the danger that the infusion fluid will reach the patient without any control. To prevent this, the pump 14 according to the invention is provided with a so called anti-free-flow hose clamp 16. In this case after opening the door 13 of the pump a closing device closes the intravenous hose off to prevent the flow.

Following this the user has to close the roller clamp 11 before the hose 12 is removed from the pump 14.

As mentioned in the introduction, this is where the potential danger of some existing arrangements and systems become obvious, since the hose 12, after its removal from the pump 14, is continued to be closed off only when the user, as already described, had already closed the roller clamp 11 on the infusion set 8. However, if the user has not closed the clamp 11 and the infusion set 8 is removed from the pump 14, the infusion solution will flow uncontrolled to the patient. Thus the patient is exposed to considerable danger due to an error in the operation of the infusion set and the pump 14.

To start up the arrangement 10 according to the invention the following steps have to be carried out:

1. Preparation of the infusion set 8:
The roller clamp 11 is closed.
The drip chamber 9 is inserted into the infusion flask 6.
The drip chamber 9 is filled.
The roller clamp 11 is opened and the infusion set is vented.
The roller clamp 11 is closed.

2. Door 13 of the pump is opened.

Figure 1B:
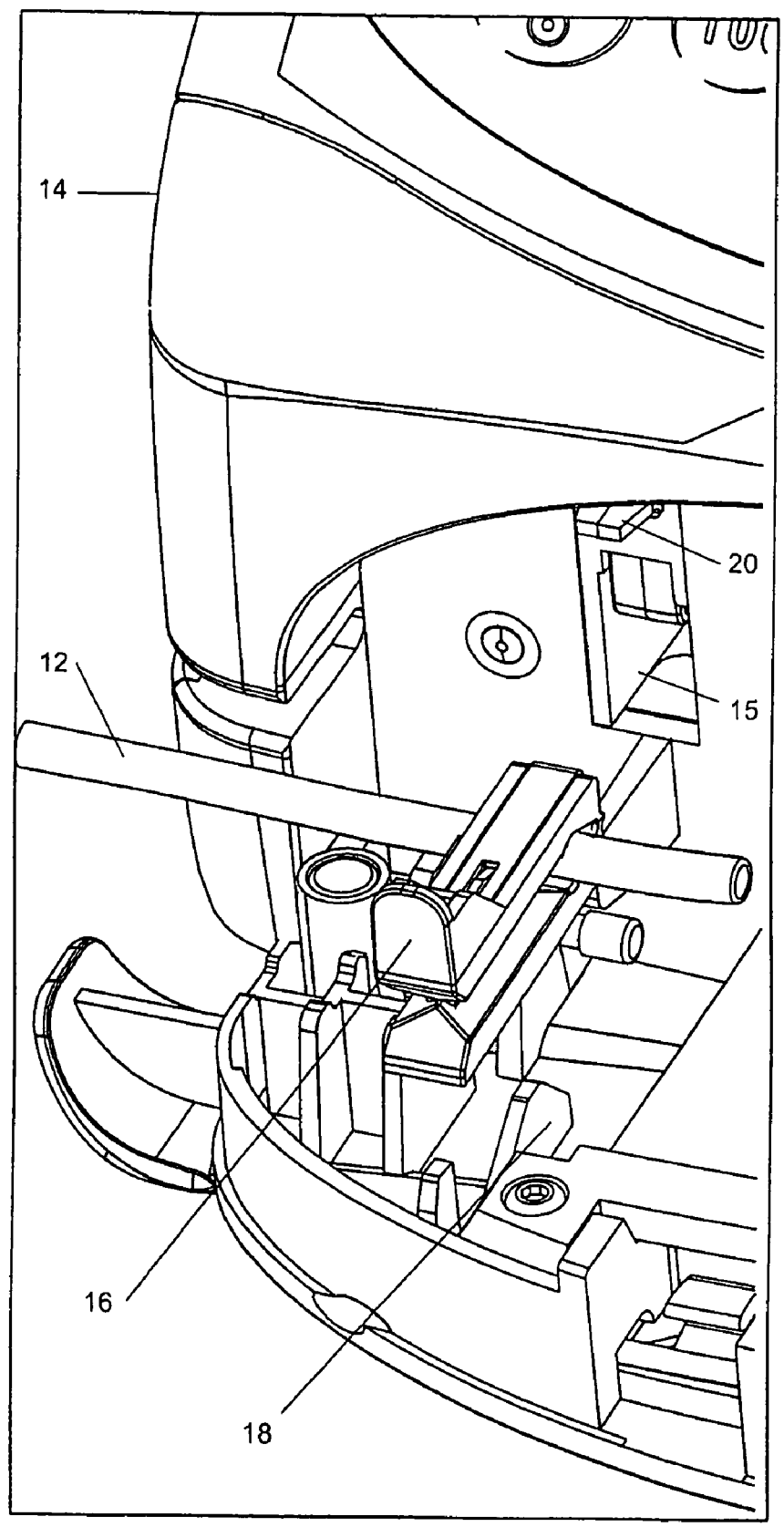
FIG. 1B is a schematic perspective illustration of a detail of FIG. 1, enlarged.

3. The intravenous hose 12 is placed horizontally into the pump 14 (see FIGS. 1A and 1B). The hose clamp 16 is placed into the receiver 15 provided for this purpose in the pump. Prior to placing the hose clamp 16 into the receiver 15 of the pump 14, the clamp 16 is opened, i.e. at this stage the hose 12 is clamped only by the closed roller clamp 11, however, the hose clamp 16 is still open and consequently its position on the hose 12 can be changed along the hose.

Figure 2:
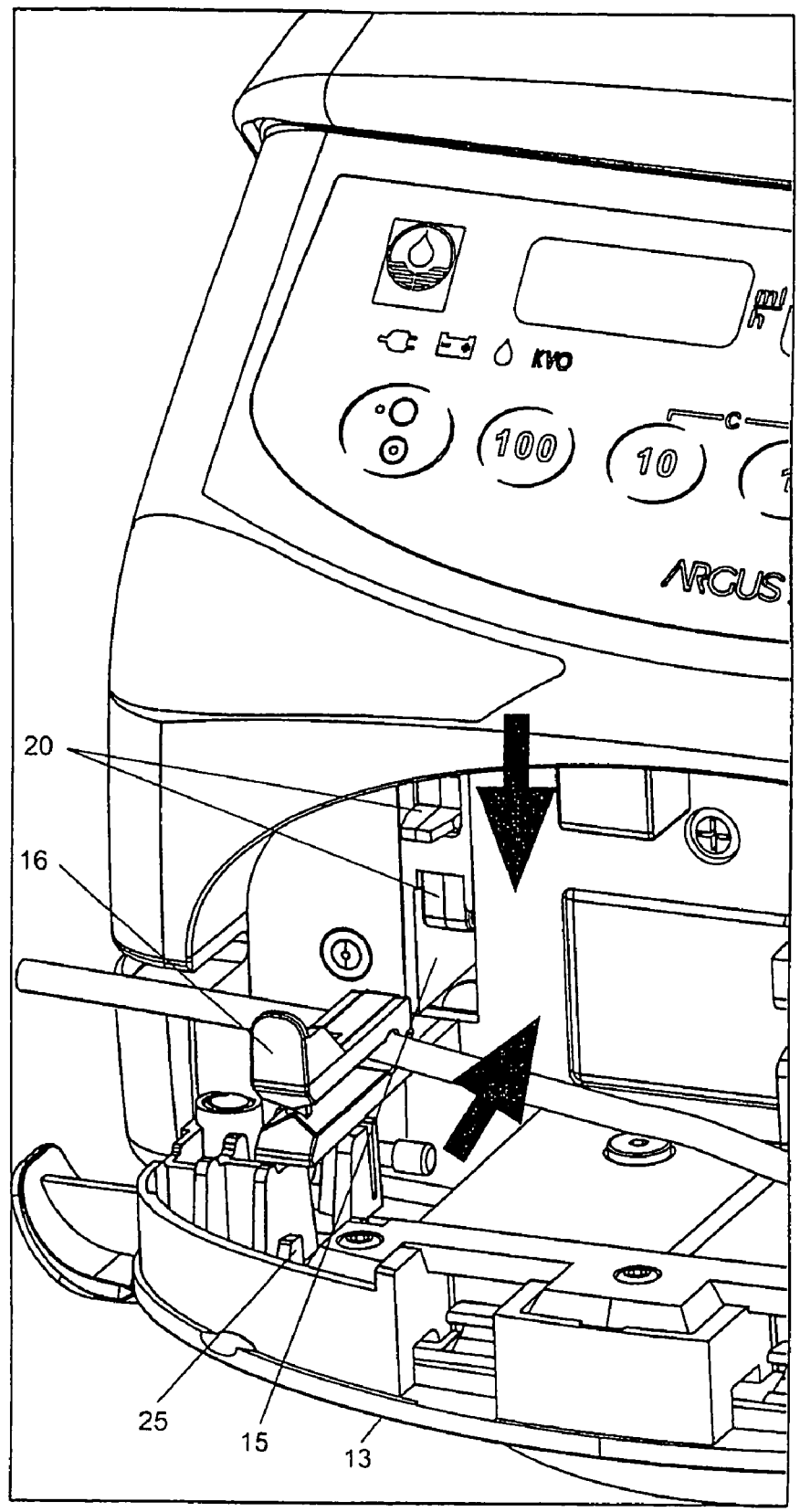
FIG. 2 is a further schematic perspective illustration of a detail of FIG. 1, enlarged.
Figure 3:
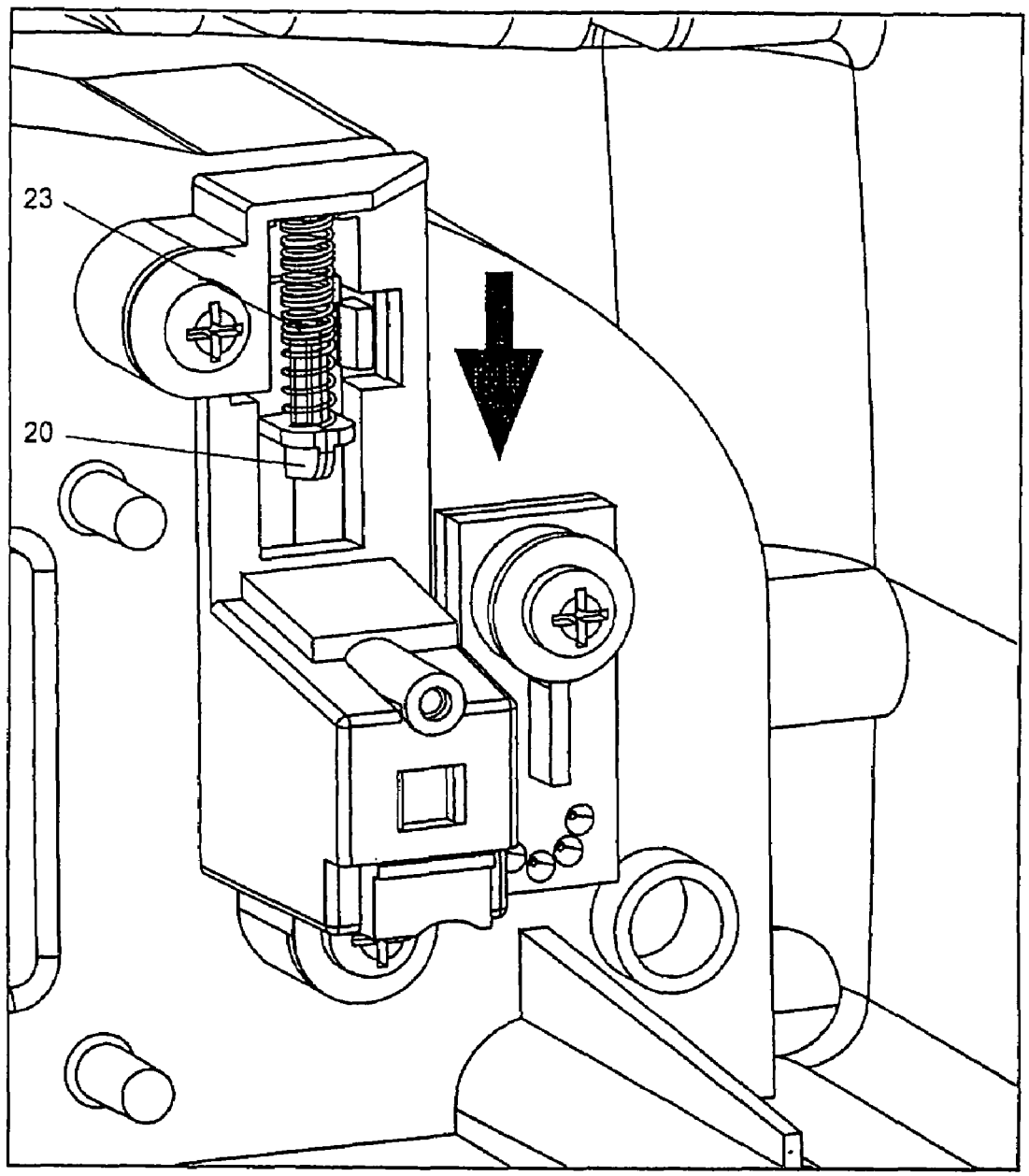
FIG. 3 is a further schematic perspective illustration of the receiver with the locking slide, in a detail from the interior of the pump.
Figure 4:
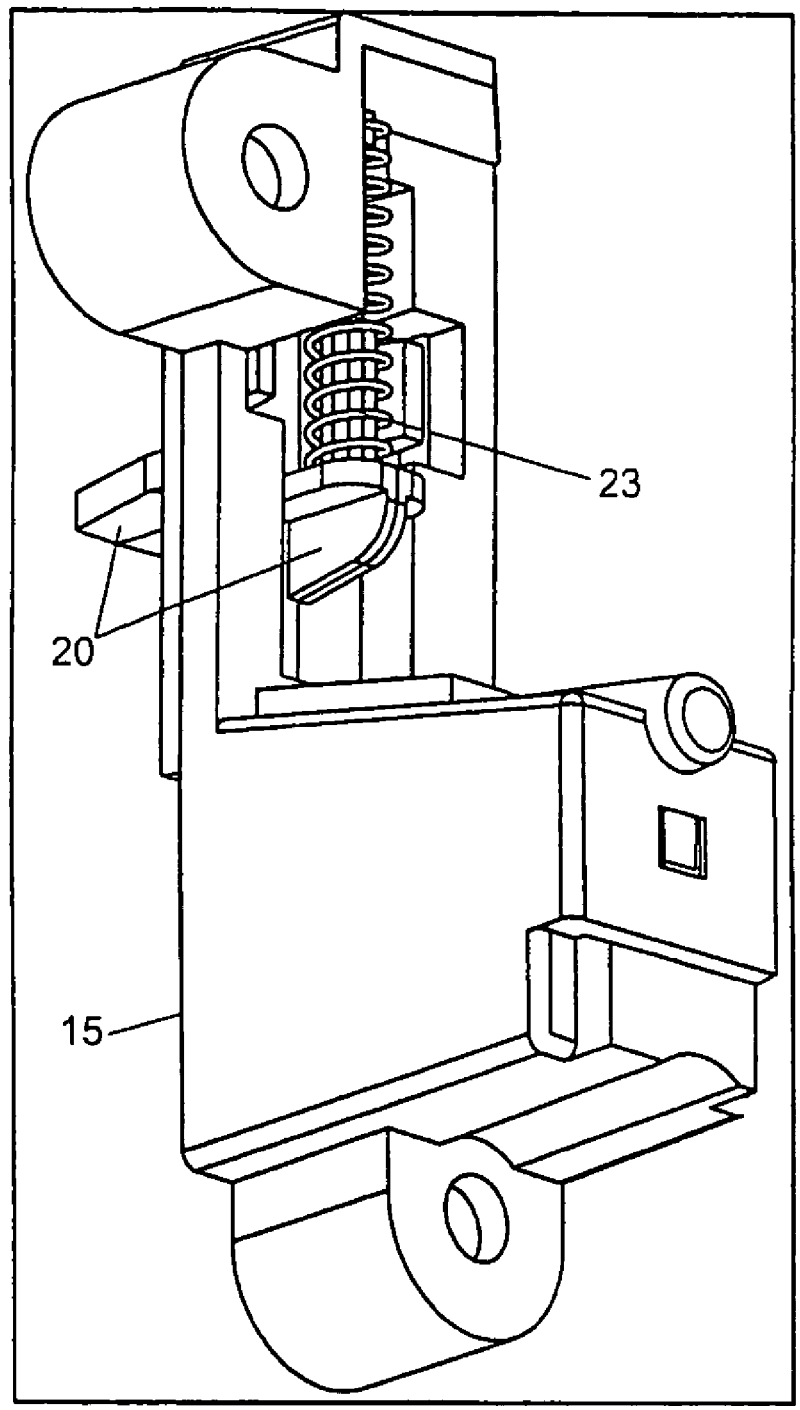
FIG. 4 is a further schematic perspective illustration of the spring-loaded locking slide.

With the clamp 16 not being inserted, the locking device of the pump 14, constructed as a locking slide 20, is biased by a spring 23 against a bottom stop, that presses the pump 14 (see FIGS. 2 and 3).

Figure 5:
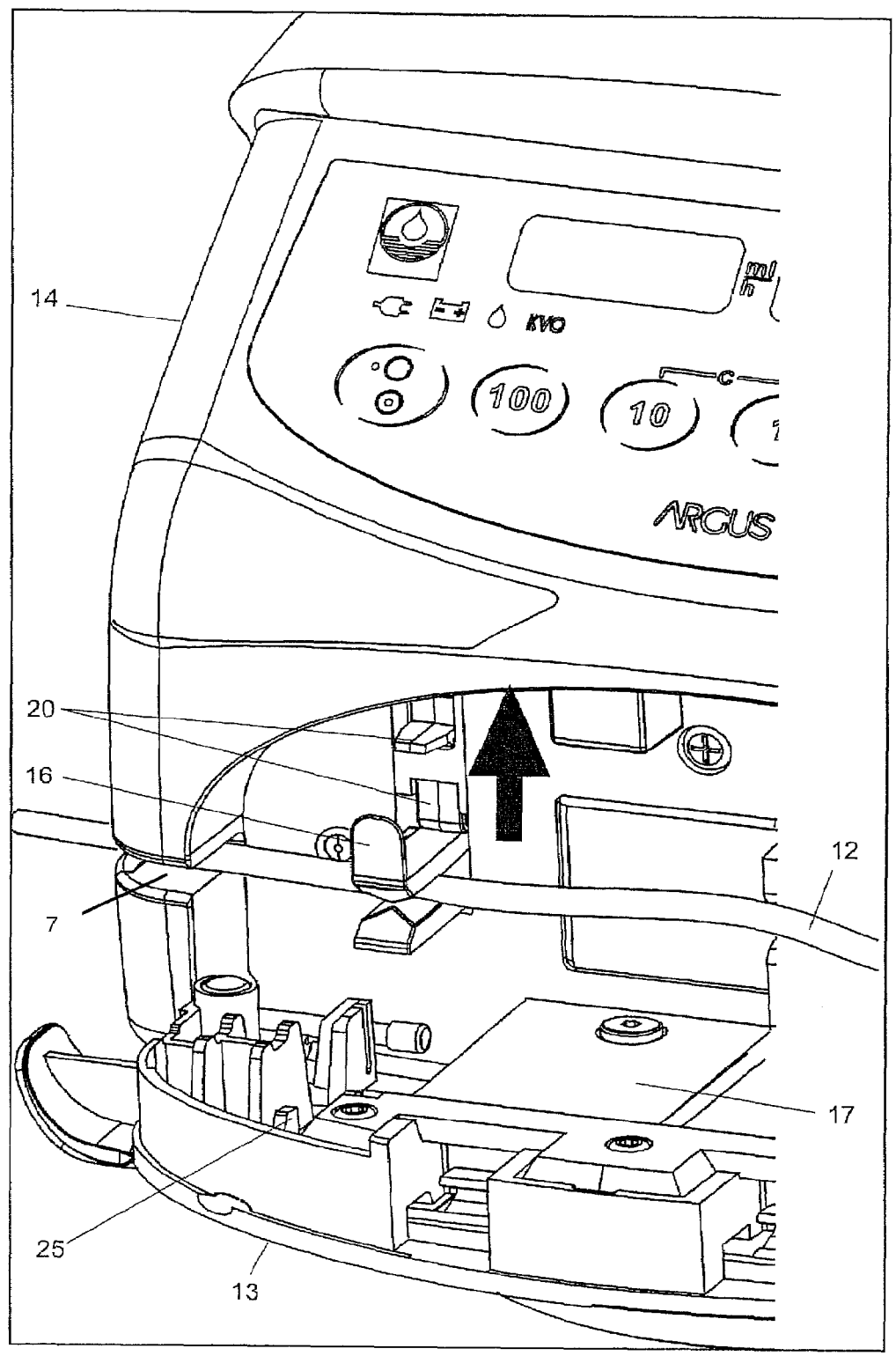
FIG. 5 is a schematic detailed view, similar to FIG. 2, but with the hose clamp locked in the receiver, with the door opened.
Figure 5A:
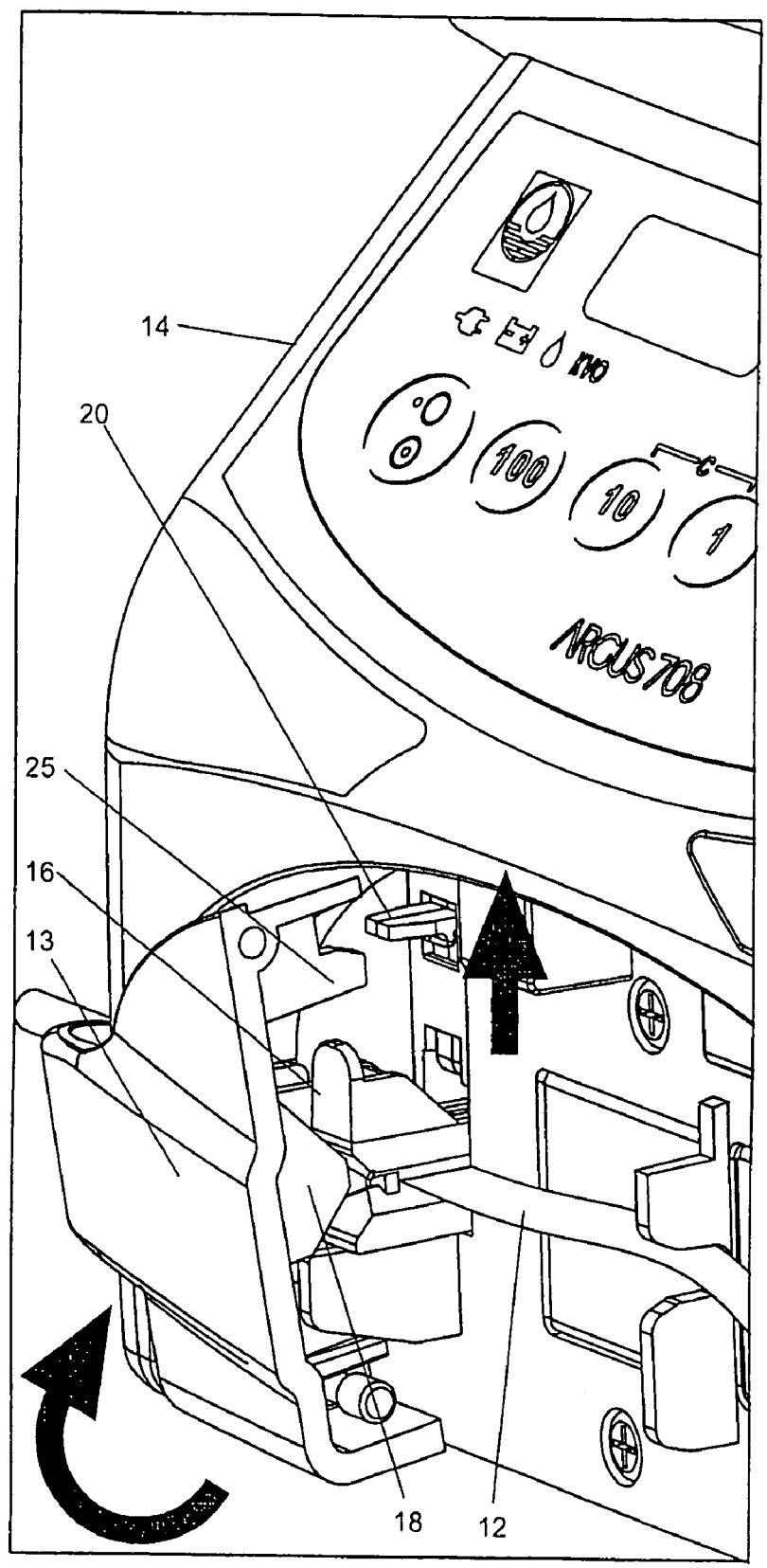
FIG. 5A is a further schematic perspective view in detail, wherein parts are removed and the door is swung upward, while the locking slide does not yet lie on the stop rib.

By inserting the hose clamp 16 into the receiver 15 of the pump 14 the locking slide 20 is pressed upwards in the direction of the arrow and retains this position (see FIGS. 5 and 5A). The locking slide 20 interacts with a stop 25 on the inside of the door 13 and slides on an inclined surface of the stop 25 when the hose clamp 16 is inserted into the receiver 15 (see FIG. 5B) At the same time the hose 12 is secured in the pump 14 and the hose clamp 16 is pushed to the back of the receiver 15. Due to this the hose clamp 16 is shifted in that region over the hose 12, in which the hose clamp 16 clamps the hose 12. FIG. 5 shows an embodiment wherein the hose 12 is positioned within horizontal hose guide 7.

Figure 5B:
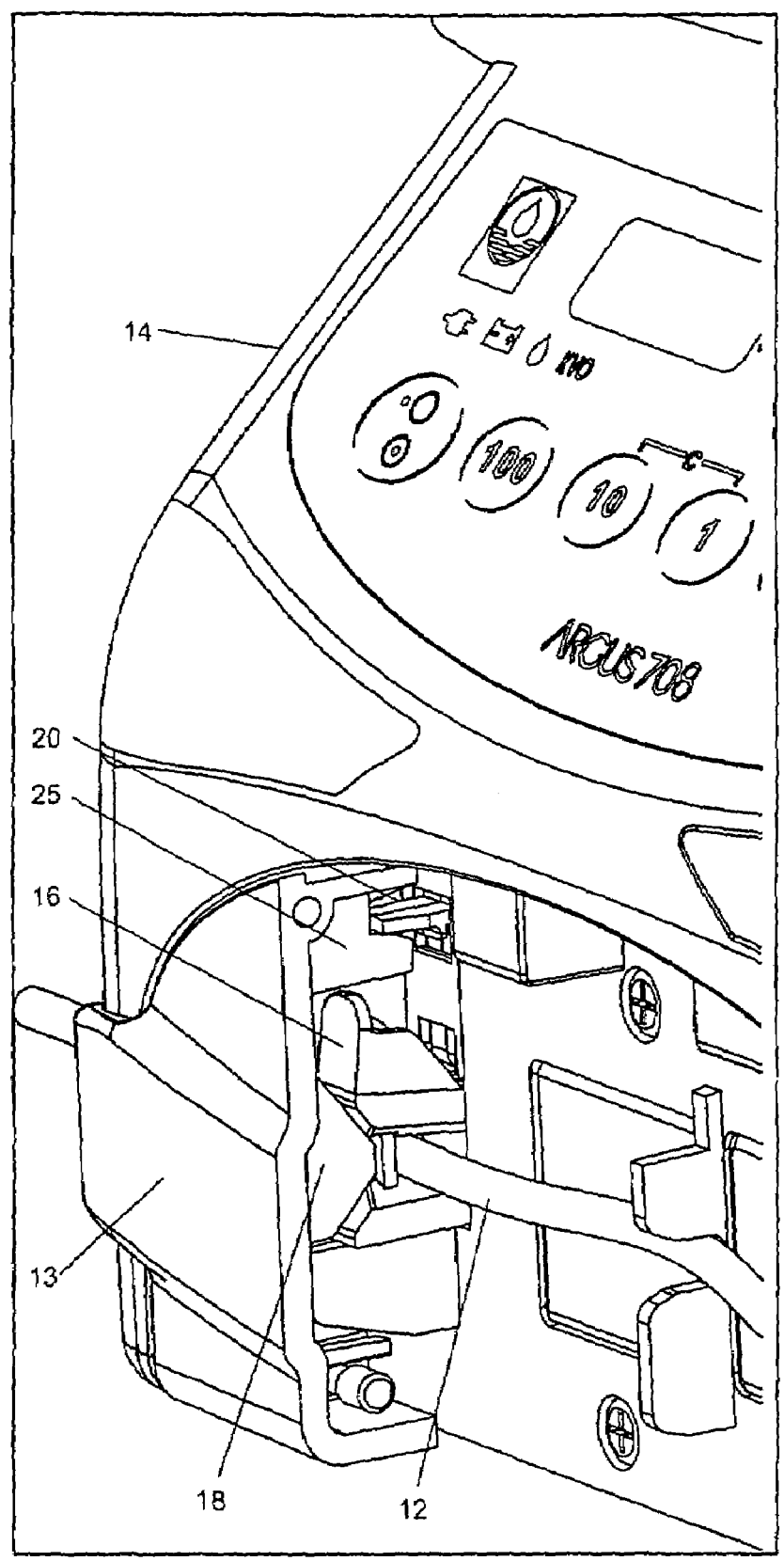
FIG. 5B is a schematic view, similar to FIG. 5A, but with the door closed and the legs of the hose clamp are spread apart by the expander rib, so that the hose can be flown through freely.

The closing of the door 13 of the pump is shown in FIGS. 5A and 5B. The door 13 of the pump can be closed only when the hose clamp 16 is inserted into the receiver and thus the locking slide 20 is pushed into its top position.

FIG. 5A shows that the door 13 can be closed now, since it is no longer blocked by the locking slide 20 abutting against the stop 25.

4. To operate the pump 14 it is necessary to open the hose clamp 16, because when the door 13 is closed the hose 12 is unclamped between a fixture 17 in the form of a pressure plate of the door 13 of the pump and the peristaltic drive, what is achieved by that after fully closing the door 13 of the pump the hose clamp 16 will be opened by an expander rib 18 situated in the door 13, as this is indicated by arrows (see FIGS. 5A and 5B).

5. After closing the door 13 of the pump the roller clamp 11 on the infusion set 8 can be opened and the set can be checked by the peristaltis of the pump 14 (the infusion solution must not flow) with regard to a total unclamping of the hose 12. The pump 14 can be started up.

To properly terminate the operation of the pump 14 the following procedure is carried out:

1. The roller clamp 11 is closed.

2. The door 13 of the pump is opened.

Figure 5C:
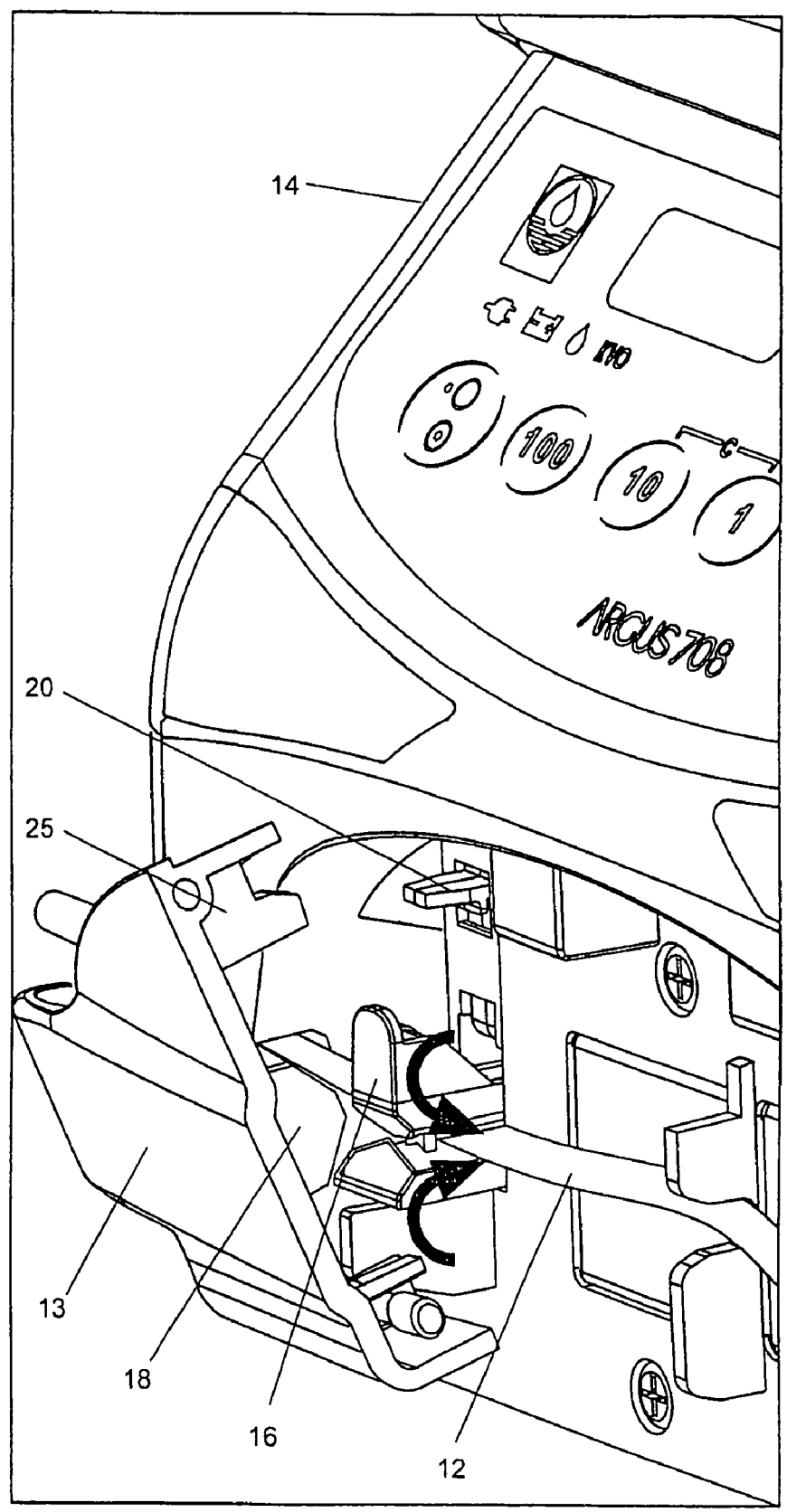
FIG. 5C is a further schematic perspective illustration in a detail, wherein the door is illustrated partly cut away during the opening process.

By opening the door 13 of the pump the hose clamp 16 is automatically closed, because the expander rib 18 of the door 13 no longer will keep the clamp 16 open. Thus the hose clamp 16 will clamp the hose 12 again automatically due to the pressure of the steel spring 21 mounted on the hose clamp 16, as this is indicated by the arrows in FIG. 5C.

3. The hose 12 with the hose clamp 16 is removed from the pump 14.

4. After opening the door 13 the hose 12 with the clamp 16 and the spring 21 can be removed from the pump 14. The hose clamp 16 with the spring 21 is removed from the receiver 15, whereby the locking slide 20 is pushed back to its initial position by the spring (FIG. 2).

Thus, when properly operated, the arrangement 10 according to the invention with the infusion pump 14 is secured against an uncontrolled flow or so called "free flow" of the infusion solution to the patient by the manually closed roller clamp 11 on the one hand and by the automatic clamping of the hose clamp 16 on the other.

The operation of the infusion pump 14 can be incorrectly terminated by various means.

If, for example, door 13 of the pump is opened without the operator previously manually closing the roller clamp 11 on the infusion set 8, the hose clamp 16, as described above, closes the hose 12 also automatically.

A further possible cause of maloperation is the starting up of the infusion pump 14 without the hose clamp 16. The decisive improvement of the arrangement 10 according to the invention is that the infusion pump 14 cannot be operated without the hose clamp 16 with the spring 21 being inserted.

Figure 6:
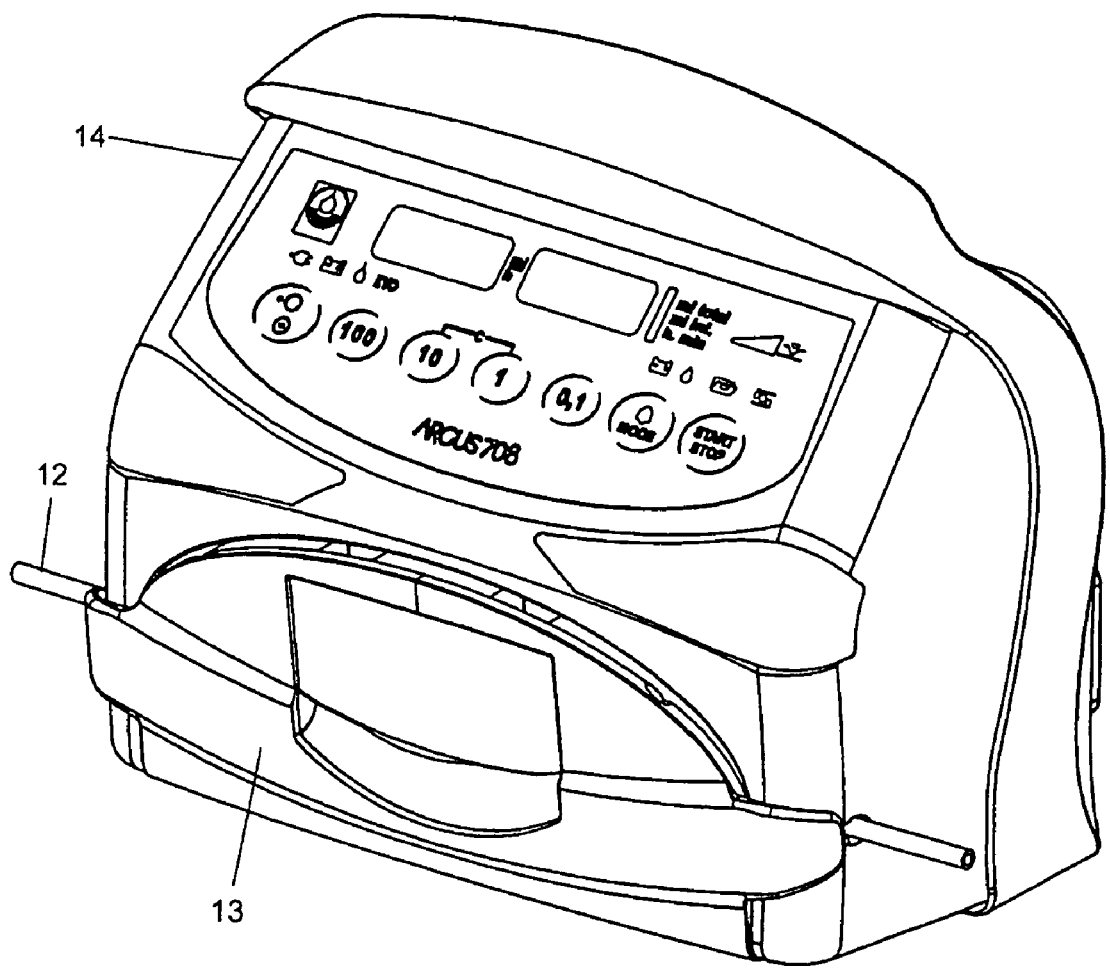
FIG. 6 is a perspective illustration of the arrangement according to the invention with the hose inserted without hose clamp, so that the door is not fully closed.
Figure 6A:
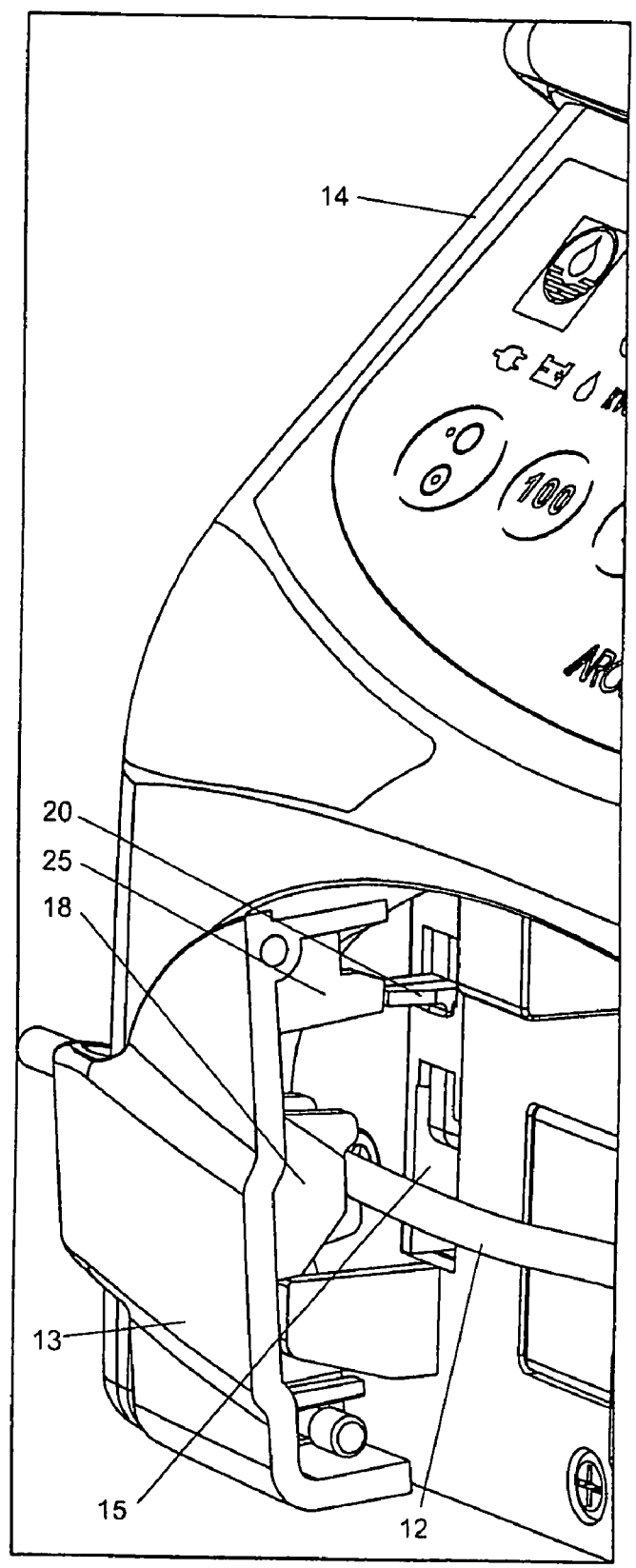
FIG. 6A is a schematic perspective illustration in detail with partly cut away door, that due to locking slide, pressing against the stop, is not closed.

This will be ensured by that the door 13 of the pump cannot be fully closed (see FIGS. 6 and 6A) if the hose clamp 16 with the spring 21 had not been inserted into the receiver 15.

If the hose clamping unit 16/21 is not inserted into the receiver 15, the locking slide 20 is pressed by the spring to the bottom end position (cf. arrow in FIG. 2). The door 13 cannot be closed because the stop rib 25 on the door 13 is exactly in the position of the locking slide 20 without the hose clamp 16 being inserted (see FIG. 6A).

Since the door 13 of the pump cannot be closed, the pump 14 cannot be operated. Thus an unintended flow of the infusion solution to the patient is not possible, because the operator cannot close the door 13 of the pump, and consequently will not open the roller clamp 11, closed after the preparation of the infusion, either.

Figure 7:
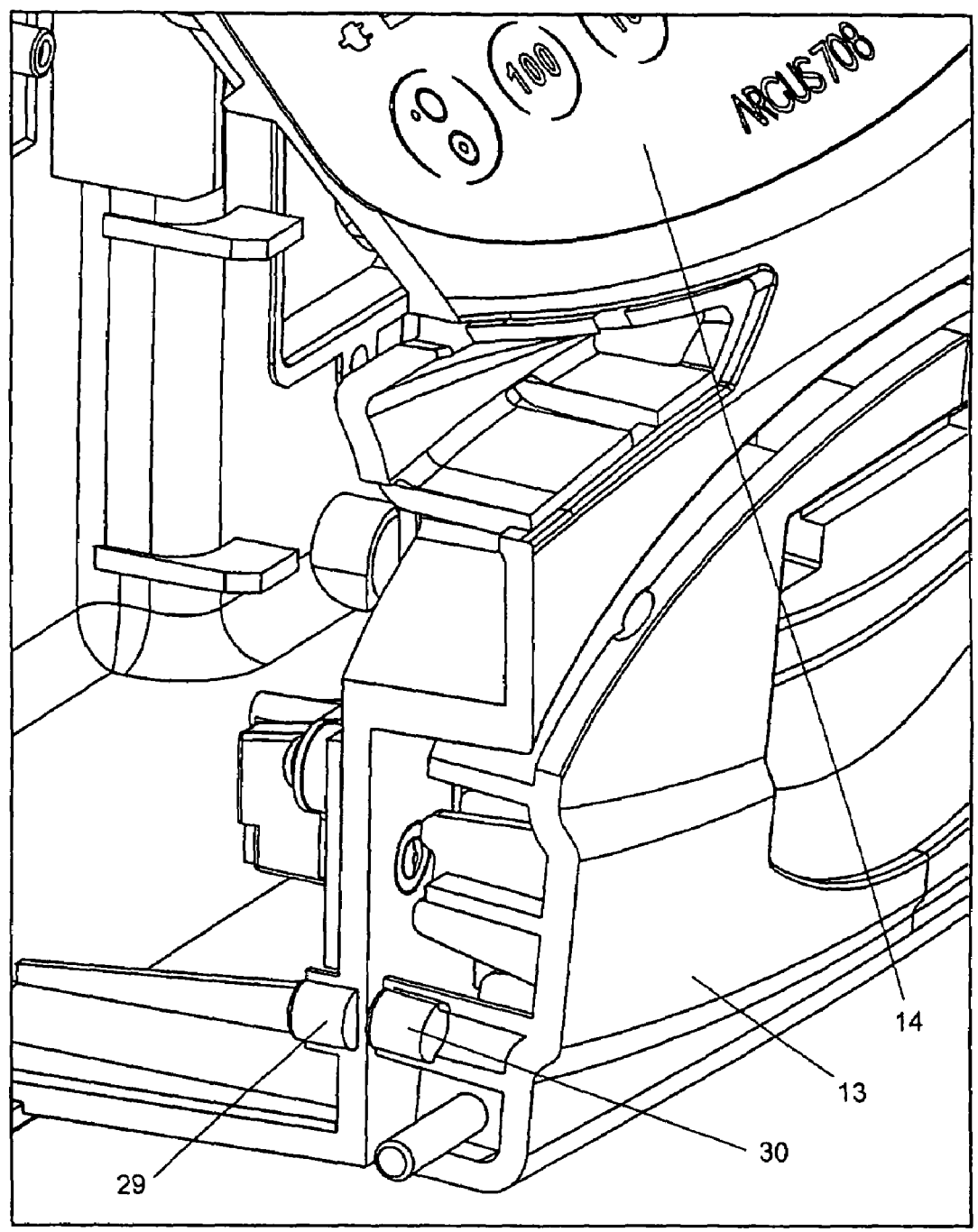
FIG. 7 is a schematic perspective illustration of a portion of the pump housing with safety magnets.

Because the pump 14 must not be stored with the door 13 open, the door is held by two magnets in a position, wherein the stop rib abuts against the locking slide 20. While one of the magnets 29, 30 is provided in the bottom corner of the housing, the other is secured in the edge region of the door, as this is illustrated in FIG. 7.

Figure 8:
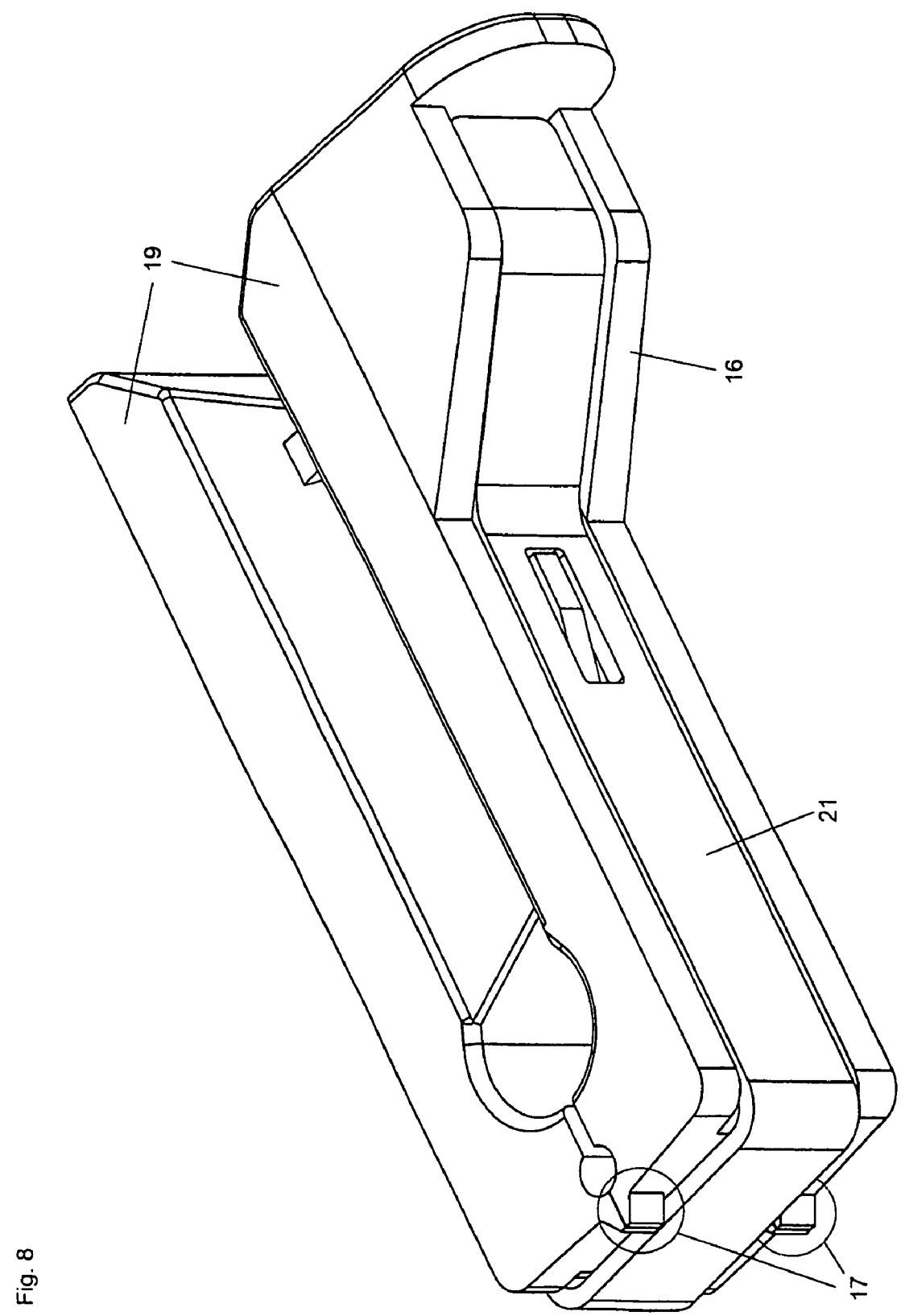
FIG. 8 is a schematic perspective illustration of the hose clamp according to the invention with a steel bending spring.

Moreover, the hose clamp 16 of the embodiment, that as clamping surfaces has legs 19 that can move relative one another about a hinge 17, is asymmetric and is enveloped on the outside surfaces of the legs by a clamping spring 21 (see FIG. 8). By virtue of this the operator cannot insert the infusion set 8 incorrectly reversed, i.e. against the direction of pumping.

Figure 9:
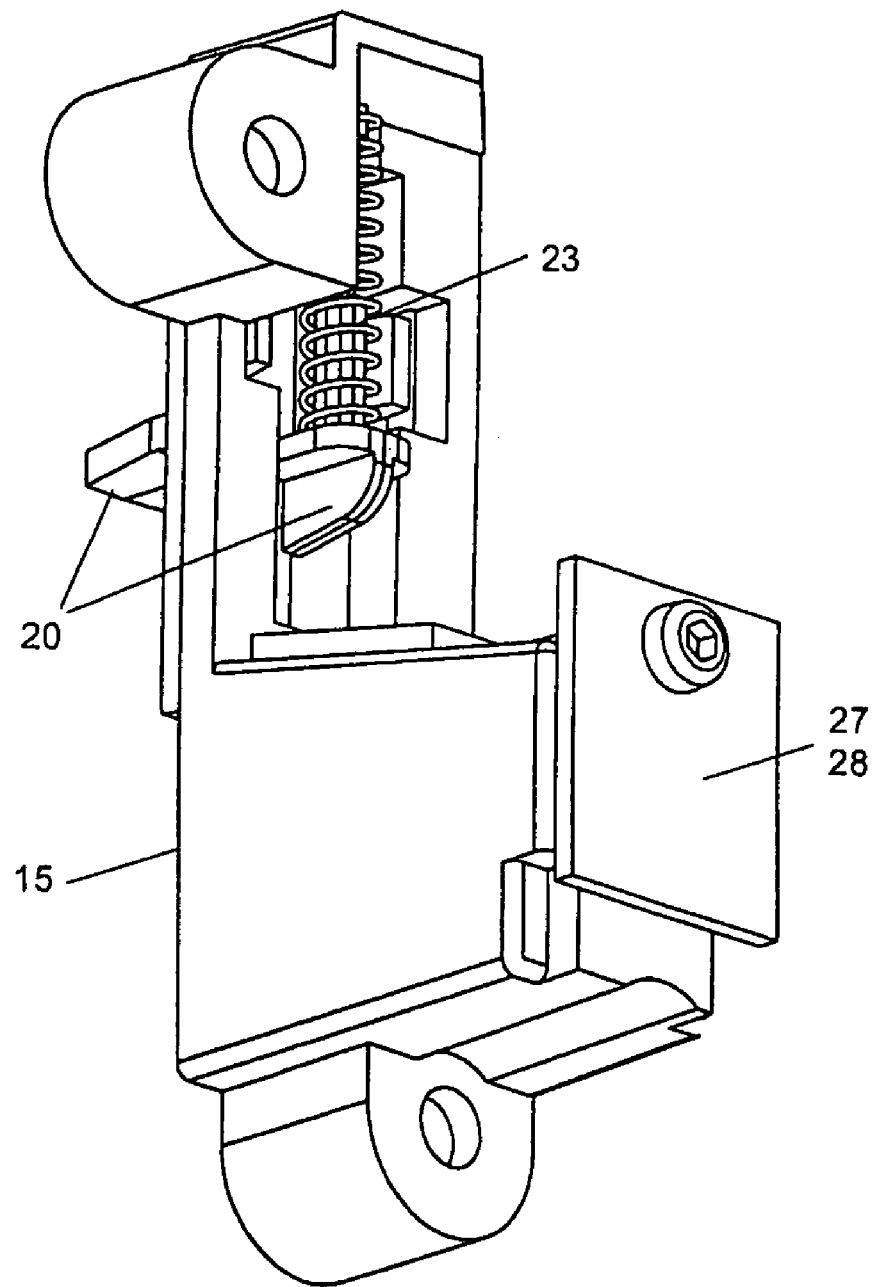
FIG. 9 is a schematic perspective illustration of the receiver or the insert module with printed circuit board and sensor.

In an advantageous manner as additional safety a printed circuit board 27 with a sensor 28 is mounted on the receiver 15, that can also be described as an insertion module (cf. FIG. 9, in which the receiver is illustrated on its own). The sensor 28 detects via the steel spring 21 on the hose clamp 16, whether the clamping unit 16/21 had been inserted into the receiver 15. The pump 14 can be started up only when the sensor 28 emits the signal "hose clamp 16 inserted".

What is claimed is:

1. An arrangement for coupling an intravenous hose having a roller clamp with an infusion pump with a housing to deliver a medicinal solution to a patient, comprising:
    a hose clamp that can be coupled with the intravenous hose and can be displaced between an open position, in which the medicinal solution can flow through the hose, and a closed position, in which the hose is closed by the hose clamp,
    a device mounted on the door or lid of the housing, that can be engaged with the hose clamp to bring it to the open position from the closed position,
    wherein the hose clamp has clamping surfaces in the form of legs which can move relative one another about a hinge, the legs being enveloped on their outside by a biased clamping spring, wherein the device is formed by an expander rib that is fastened on the inside of the door and can be brought into engagement with the legs of the hose clamp so that to produce the open position after closing the door to expand the legs,
    wherein the housing has a receiver, into which the hose clamp can be snapped,
    and wherein a locking device is present in the housing that prevents the closing of the door if the hose clamp is not inserted into the receiver and permits the closing of the door when the hose clamp is fully inserted wherein the locking device is formed by a locking slide biased by means of a spring, said locking slide interacting with a stop on the inside of the door and slides on an inclined surface of the stop when the hose clamp is inserted into the infusion pump to bring about the open position and the door is closed.

2. The arrangement according to claim 1 wherein in the region of the receiver a printed circuit board with a sensor is mounted, that detects whether the hose clamp is pushed in or not.

3. The arrangement according to claim 1 wherein for the storage of the infusion pump when not in use a securing by magnets is provided, that holds the door closed, while the stop is provided on the locking slide.

4. The arrangement according to claim 1 wherein the hose clamp can be snapped into the receiver in a form-locking manner.

5. The arrangement according to claim 1 wherein horizontal hose guides are provided in the housing both on the entry and outlet sides.

6. The arrangement according to claim 1 wherein the door extends almost over the entire width of the housing and can be pivoted upwards into the closed position.

7. The arrangement according to claim 1 wherein the anti-free-flow hose clamp is positioned past the entry into the housing and before the drive of the infusion pump and is made from an injection moulded piece, the legs of which are enveloped by a metal clamping spring.

8. The arrangement according to claim 1 wherein the hose comprises PVC or PVC-free having a Shore hardness A 75 to 85, an inside diameter of 3.0 mm and an outside diameter of 4.10 mm, and the clamping force of the hose clamp is minimum 10 N.

9. The arrangement according to claim 1 comprising a volumetric infusion pump with a peristaltic drive.

10. The arrangement according to claim 1 wherein for the storage of the infusion pump when not in use a securing by magnets is provided, that holds the door closed, while the stop is provided on the locking slide.

11. The arrangement according to claim 1 wherein the hose clamp can be snapped into the receiver in a form-locking manner.

12. The arrangement according to claim 1 wherein horizontal hose guides are provided in the housing both on the entry and outlet sides.

13. The arrangement according to claim 1 wherein the door extends almost over the entire width of the housing and can be pivoted upwards into the closed position.

14. The arrangement according to claim 1 wherein the anti-free-flow hose clamp is positioned past the entry into the housing and before the drive of the infusion pump and is made from an injection moulded piece, the legs of which are enveloped by a metal clamping spring.

15. The arrangement according to claim 1 wherein the hose comprises PVC or PVC-free having a Shore hardness A 75 to 85, an inside diameter of 3.0 mm and an outside diameter of 4.10 mm, and the clamping force of the hose clamp is minimum 10 N.

16. The arrangement according to claim 1 comprising a volumetric infusion pump with a peristaltic drive.

17. The arrangement according to claim 1, wherein in the region of the receiver a printed circuit board with a sensor is mounted, that detects whether the hose clamp is pushed in or not; and wherein for the storage of the infusion pump when not in use a securing by magnets is provided, that holds the door closed, while the stop is provided on the locking slide; and wherein the hose clamp can be snapped into the receiver in a form-locking manner; and wherein horizontal hose guides are provided in the housing both on the entry and outlet sides; and wherein the door extends almost over the entire width of the housing and can be pivoted upwards into the closed position; and wherein the anti-free-flow hose clamp is positioned past the entry into the housing and before the drive of the infusion pump and is made from an injection moulded piece, the legs of which are enveloped by a metal clamping spring; and wherein the hose comprises PVC or PVC-free having a Shore hardness A 75 to 85, an inside diameter of 3.0 mm and an outside diameter of 4.10 mm, and the clamping force of the hose clamp is minimum 10 N; and further comprising a volumetric infusion pump with a peristaltic drive.

* * * * *